United States Patent [19]

Dieter

[11] Patent Number: 5,716,329
[45] Date of Patent: Feb. 10, 1998

[54] DISPOSABLE EXPANDABLE SPECULUM

[76] Inventor: Michael A. Dieter, 2117 S. Newer Ct., Veradale, Wash. 99037

[21] Appl. No.: 724,555

[22] Filed: Sep. 30, 1996

[51] Int. Cl.$^6$ .................... A61B 1/00; A61B 1/303
[52] U.S. Cl. .................... 600/210; 600/201; 600/184; 600/245
[58] Field of Search .................... 600/207, 213, 600/226, 203, 191–193, 234, 245, 201, 227, 184; 606/208, 213

[56] References Cited

U.S. PATENT DOCUMENTS

| | | | |
|---|---|---|---|
| 1,624,716 | 4/1927 | Cerbo . | |
| 2,548,602 | 4/1951 | Greenburg | 600/207 |
| 3,044,461 | 7/1962 | Murdock | 128/4 |
| 3,532,088 | 10/1970 | Fiore | 600/213 |
| 3,675,641 | 7/1972 | Fiore | 600/184 |
| 3,704,712 | 12/1972 | Giesy et al. | 128/345 |
| 3,744,481 | 7/1973 | McDonald | 600/213 |
| 3,774,596 | 11/1973 | Cook | 128/5 |
| 3,782,370 | 1/1974 | McDonald | 128/20 |
| 3,831,587 | 8/1974 | Boyd | 600/207 |
| 4,502,468 | 3/1985 | Burgin | 128/18 |
| 4,601,713 | 7/1986 | Fuqua | 604/280 |
| 4,638,792 | 1/1987 | Burgin | 128/6 |
| 4,690,132 | 9/1987 | Bayer et al. | 128/4 |
| 4,984,564 | 1/1991 | Yuen | 128/20 |
| 4,994,070 | 2/1991 | Waters | 606/191 |
| 5,049,131 | 9/1991 | Deuss | 604/96 |
| 5,163,418 | 11/1992 | Fraden | 600/203 |
| 5,176,659 | 1/1993 | Mancini | 604/280 |
| 5,178,133 | 1/1993 | Pena | 600/203 |
| 5,192,307 | 3/1993 | Wall | 623/1 |
| 5,249,568 | 10/1993 | Brefka | 600/184 |
| 5,377,667 | 1/1995 | Patton et al. | 128/3 |
| 5,545,122 | 8/1996 | Spruill | 600/207 |

*Primary Examiner*—Richard J. Apley
*Assistant Examiner*—Denise Pothier
*Attorney, Agent, or Firm*—Wells, St. John, Roberts, Gregory & Matkin PS

[57] ABSTRACT

An expandable speculum is described which may be provided in kit form. The speculum includes a handle with an integral eyepiece. A set of first elongated tubular members, each releasably connectable to the handle adjacent the eyepiece are formed of a substantially rigid material. Each includes an external surface and an internal bore formed along a longitudinal axis. A selected one of the tubular members may be selected and attached to the handle. The elongated tubular members in the set include various lengths and cross-sectional dimension at the external surfaces thereof to permit selection according to use and patient physiology. Elastic tubular sheaths are disposed axially over the external surfaces of the first elongated tubular members and are radially inflatable with respect to the first tubular members and said longitudinal axis in response to application of fluid pressure. Any one of the tubular members is releasably attachable to the handle in such a manner that the eyepiece is in axial alignment with the internal tube bore. Any one member and the sheath mounted thereto may be inserted in an orifice defined by supportive tissues, with the sheath in a deflated state, the sheath being inflatable in the orifice to engage and expand against the supportive tissues and thereby secure the speculum axially within the orifice while permitting angular movement of the handle and first tubular member with respect to the inflated sheath and the engaged supportive tissue.

24 Claims, 11 Drawing Sheets

DISPOSABLE EXPANDABLE SPECULUM

TECHNICAL FIELD

The present invention relates to instruments facilitating inspection, diagnostic procedures, and treatment through body passages, and more particularly to specula having capability of expansion following insertion into a body passage.

BACKGROUND OF THE INVENTION

There has been little advancement in the development of specula, especially of the type used for vaginal examination and medicating. Metal, autoclavable duck-bill specula are conventionally used for gynecological examination and treatment. These units, with exposed joints, sharp edges, and cold metal are universally disliked and feared by patients. The hinged joints and blade edges could easily and often did pinch, scrape, or otherwise traumatize the supporting tissues in the area being examined. Further the instruments are typically cold and extremely uncomfortable.

In an attempt to eliminate the need to sterilize, plastic specula have been developed. These forms although usually warmer than metal specula, were still configured after the same duck-bill shape, with the blades opening and closing along separation lines that could easily allow tissue to be pinched on closure, or that would scrape tissues painfully on rotation.

Another difficulty with existing forms of specula, is that such apparatus require the use of one hand to hold the device in place, thus limiting the use of the other hand. Thus an attendant is often needed, and the examination or treatment becomes obstructed by another person's hands and arms. This is also inefficient and raises costs for otherwise relatively inexpensive procedures.

Yet further difficulty with existing forms of specula comes from the typically opaque nature, especially in the metal specula, of the specula blades. The only area available for inspection when a speculum is in use, is the open end, for cervical examination, and the vaginal wall areas between the opened blades. Thus for a thorough examination of the vaginal walls, the speculum must be rotated. This causes the edges of the blades (even if closed) to scrape against the sensitive tissues, often causing severe discomfort and even occasional lacerations. Lacerations of the vaginal walls are potentially serious due to susceptibility of that area to infection.

Sufficient lighting of the subject area for examination is another area of difficulty, since typical specula are not equipped with illumination devices. Light must be directed from another source, often a penlight held by the attendant's free hand. This is inadequate at best because the light reflects off the speculum blades and will often obstruct clear view of the area to be examined or treated. Also the need to use the free hand to hold a light is a problem since the free hand is often needed to hold and manipulate other instruments. In addition a flashlight properly held to directly light the area for examination or treatment necessarily obstructs the direct view of the attendant, so only indirect lighting can be used. Head mounted lights have been used as a partial solution to this problem, but the reflection along the speculum blades and the inability to direct the light properly remain as frustrating problems for the attendant.

The present invention solves the above problems by providing a more comfortable, disposable, inflatable, transparent, and internally lighted speculum that can be provided in many sizes of both diameter and length. The disposable nature of the present speculum enables reliable, safe use. The present speculum includes a soft, inflatable sleeve that will accommodate any intermediate size and expand to gently engage and secure the speculum inspection tube in place, freeing both hands of the attendant. The sleeve and tube are both transparent to enable the attendant to not only view the tissues adjacent the open speculum end, but to see the tissues along the full length of the vaginal canal. Internal lighting, based on fiber optic principles allows for direct lighting of the area at the end of the speculum, thus leaving an unobstructed, clear view of the adjacent tissues. Still further, the present speculum does not make use of separable blades. Only a soft, continuous inflatable sleeve engages the vaginal walls, so no pinching or scraping will occur. The inflatable nature of the sleeve adds still further advantages in that the tube, located centrally within the airspace within the inflated sleeve, can be easily maneuvered angularly within the vagina with little if any discomfort to the patient. These and still further objects and advantages will become evident from the following description of a preferred embodiment.

BRIEF DESCRIPTION OF THE DRAWINGS

Preferred embodiments of the invention are described below with reference to the following accompanying drawings.

FIGS. 9–12 are diagrammatic views illustrating use of the present speculum for vaginal inspection; and FIG. 13 is a view showing a kit including a selection of tube and styler sizes, each capable of use with a single handle.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

A preferred form of the present speculum is shown in the drawings and is generally labeled therein by the reference numeral 10. The speculum is intended to be provided for numerous medical uses, but will most commonly be used as a vaginal speculum. The vaginal speculum configuration is therefor described herein. Other quite conceivable uses, some requiring modification of scale or structure yet incorporating features common to the present invention, include bullet and stab wound inspection and treatment, urethroscopy, proctoscopy, incision retraction, venous dilation, esophageal dilation, bronchial dilation, nasal and aural canal inspection, or other uses that may take advantage of structure common to the present invention.

The speculum 10 may be provided in several sizes as a vaginal speculum. Preferably, it will initially be provided in kit form, to accommodate several patient sizes. Examples of various sizes in an exemplary kit are shown by way of example in FIG. 13. A single handle element 33 is shown in FIG. 13 for use with any one of a plurality of tubular members 16a, 16b, or 16c used for insertion and dilation of an orifice. Several stylets 53a, 53b, and 53c that are used to facilitate insertion may also be provided, one for each size tube.

Thus the present speculum may be provided with interchangeable parts in kit form. Further, the present speculum, once the handle portion is purchased, can be supplied with disposable tubes acquired separately from the handle. Alternatively, the tubes can be used separately from the handle, with or without a stylet. As a further alternative, the speculum can be produced with an integral tube and handle, with or without a removable stylet.

Referring in more detail to structural features of a preferred embodiment, attention is drawn to FIGS. 1–5 of the drawings. There, an expandable speculum 10 is shown in which a first elongated tubular member 16 is formed of a substantially rigid material and includes an external surface 17 and an internal surface 18 defining an axial bore formed along a central longitudinal axis. The tubular member 16 extends along the central axis from an annular open leading or forward end 19 to a rearward end 20 that is also open. An open central bore extends the full length of the tubular member from forward end 19 to rearward end 20.

The length and diameter of the tubular member 16 can be varied according to need. Also, the material selected for the tubular member is preferably an appropriate substantially rigid, transparent plastic material. The tubular member may thus be injection molded, or extruded and cut from tube stock to desired lengths. The tube walls may be relatively thin to promote a degree of flexibility and to minimize the outside diameter while maximizing the interior bore diameter to facilitate inspection and instrument access when in use.

One preferred material for use in the tube is acrylic plastic, since such plastic is relatively rigid, can be injection molded or extruded, and can have excellent light conductive, fiber optic properties most suitable for use with the present invention. Another appropriate tube material is produced under the trademark "LEXAN." "Lexan" plastic also has similar useful properties.

Figure 7:
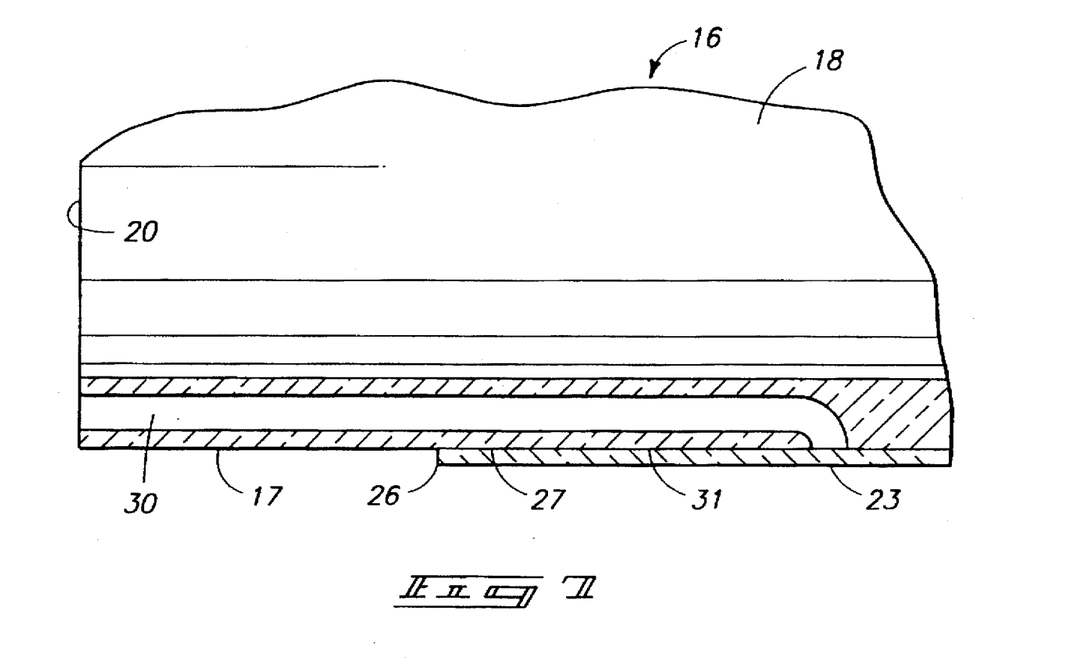
FIG. 7 is an enlarged fragmented view of a rearward area of the tube and sleeve indicated within the circle labeled 7 in FIG. 5.

The rearward end 20 of the first tubular member 16 is provided with at least one fluid passage 30 (FIGS. 5, 7) extending from the end 20 to a discharge hole in the external surface 17. The hole is located to communicate within a space 31 between the external tube surface 17 and the internal surface of the sheath 23 described below. Further, the tube 16 is provided with a light emitting or diffusion surface 52 at its forward end 19 to emit light carried along the thickness of the tube in the manner of fiber optics, from a source located in the handle also to be described below.

In a preferred form, an elastic tubular sheath 23 (FIG. 5) is disposed axially over the external surface of the first elongated tubular member 16. Installed, the sheath includes an inner surface 28 that normally fits snug against the external surface 17 of the first tubular member 16 leaving the forward end 19 open. It also has an external surface 29 that, with surface 28 defines the sheath thickness dimension. The sheath 23 is radially inflatable with respect to the first tubular member and the longitudinal axis in response to application of fluid pressure (application of which will be described in further detail below).

Figure 11:
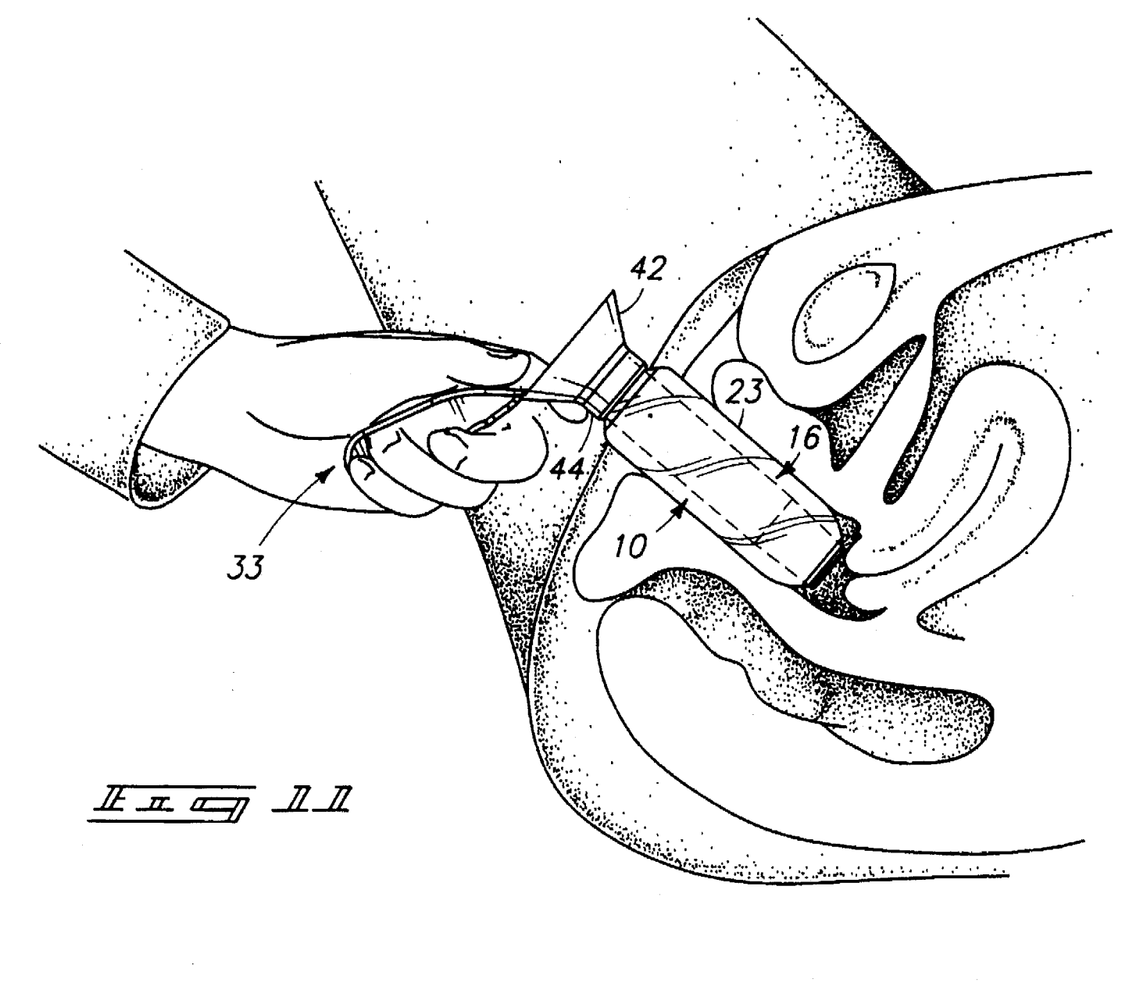

The first tubular member and sheath are preferably configured to enable insertion with the sheath 23 in a deflated state into an orifice defined by supportive tissues (FIG. 9). The sheath may be selectively inflated in the orifice (FIGS. 11 and 12) to engage and expand against tissues surrounding the orifice and thereby secure the speculum within the orifice while permitting angular movement of the first tubular member with respect to the inflated sheath and the supportive tissue.

The sheath is advantageously formed of a fluid impervious, elastic material such as latex. A thickness preferred for use with the present invention will be similar or identical to that used in condoms. Latex has been found to have sufficient elastic properties and can be made sufficiently impermeable to pressurized fluid such as air to function well as sheath material. However other materials such as highly elastic plastic may also be used effectively. The term "latex" should thus be understood as including any material having latex properties.

Figure 6:
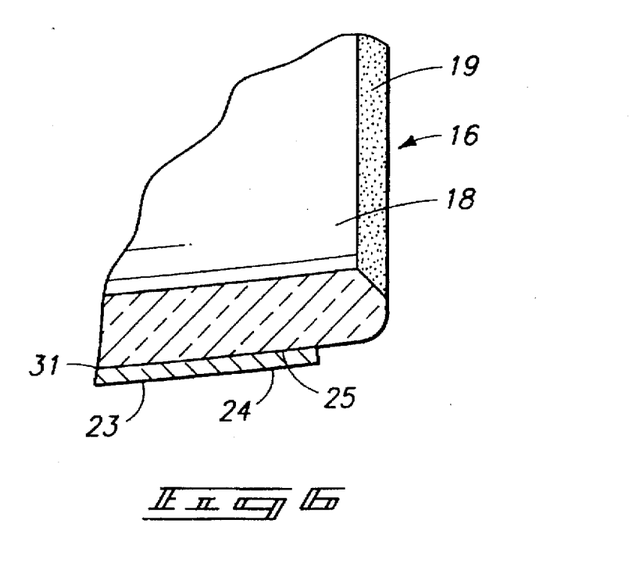
FIG. 6 is an enlarged fragmented view of a forward area of the tube and sleeve indicated within the circle labeled 6 in FIG. 5.

The sheath 23 includes a forward end 24 and a rearward end 26. At least the forward end 24, and preferably both ends are sealed at 25 and 27 (FIGS. 6, 7) respectively to the first tubular member, preferably at locations axially inward and adjacent the tube ends 19, 20. Such inward spacing of the seals minimizes the possibility of the sheath being inflated and ballooning axially outward beyond the tube ends. The latex material may be secured by common techniques or materials such as sonic welding, by heat staking, or by adhesives, to produce a fluid impervious bladder with the tubular member 16 at the core.

The sealed ends of the sheath produce the space 31 between the inner surface of the sheath and the outward surface of the tube. This is the space that becomes filled with fluid (preferably air) to expand the sheath radially during operation. Such fluid is carried to and from the space 31 by way of the passages 30 formed in the first tubular member 16.

The handle 33 briefly mentioned above is, in a preferred form, releasably attachable to the first tubular member 16. The handle may be a non-disposable part of the device, and be used repeatedly with routine cleaning and disinfecting practices since it is not exposed to internal tissues and therefor does not require sterilization. In a preferred form, the handle is formed of an appropriate health approved injection molded plastic. Alternatively, the handle may be formed of metal, though plastic is preferred due to ease of manufacture, and the warmer "feel" plastics provide over unheated metals.

The handle includes a pump 34 (FIG. 8) and a fluid supply line 39 that is extendable to the sheath for selectively inflating the sheath. The supply line 39 communicates with the fluid passages 30 in the first tubular member 16 when the tube is mounted to the handle. A release valve 40 is connected to the pump 34 and fluid supply line 39 and is positioned on the handle for selective operation to deflate the sheath.

As an alternative, the handle may be produced without a pump, and an appropriate fitting such as a typical hose barb (not shown) may be supplied either on the first tubular member 16, or on the handle 33 for connection to an alternate source of fluid pressure, such as a common blood pressure cuff bulb pump.

In a preferred form, however, the pump 34 is integrated with the handle for convenience to the user, and may be constructed in a relatively standard form. Here the pump is exemplified as a simple air pump, including a manually actuated plunger 35, connected to a piston 36. The piston slides within a cylinder 37 mounted within the handle. Conventional one way valves 38 are mounted for communication with the cylinder 37. One of the valves will allow air into the cylinder, the other will allow pressurized air into the fluid line 39. Thus pumping action of the cylinder will cause air to be drawn into the cylinder as the piston extends, and will force air into the supply line as the plunger is retracted. An ordinary return spring may be provided within the cylinder to return the piston and plunger to their starting positions shown in FIG. 8.

It is pointed out that the manual pump described above is merely exemplary, and that other forms of pump may be used. For example, an electric motor driven pump (not shown) could be used in the handle or separately therefrom to supply fluid pressure.

Figure 1:
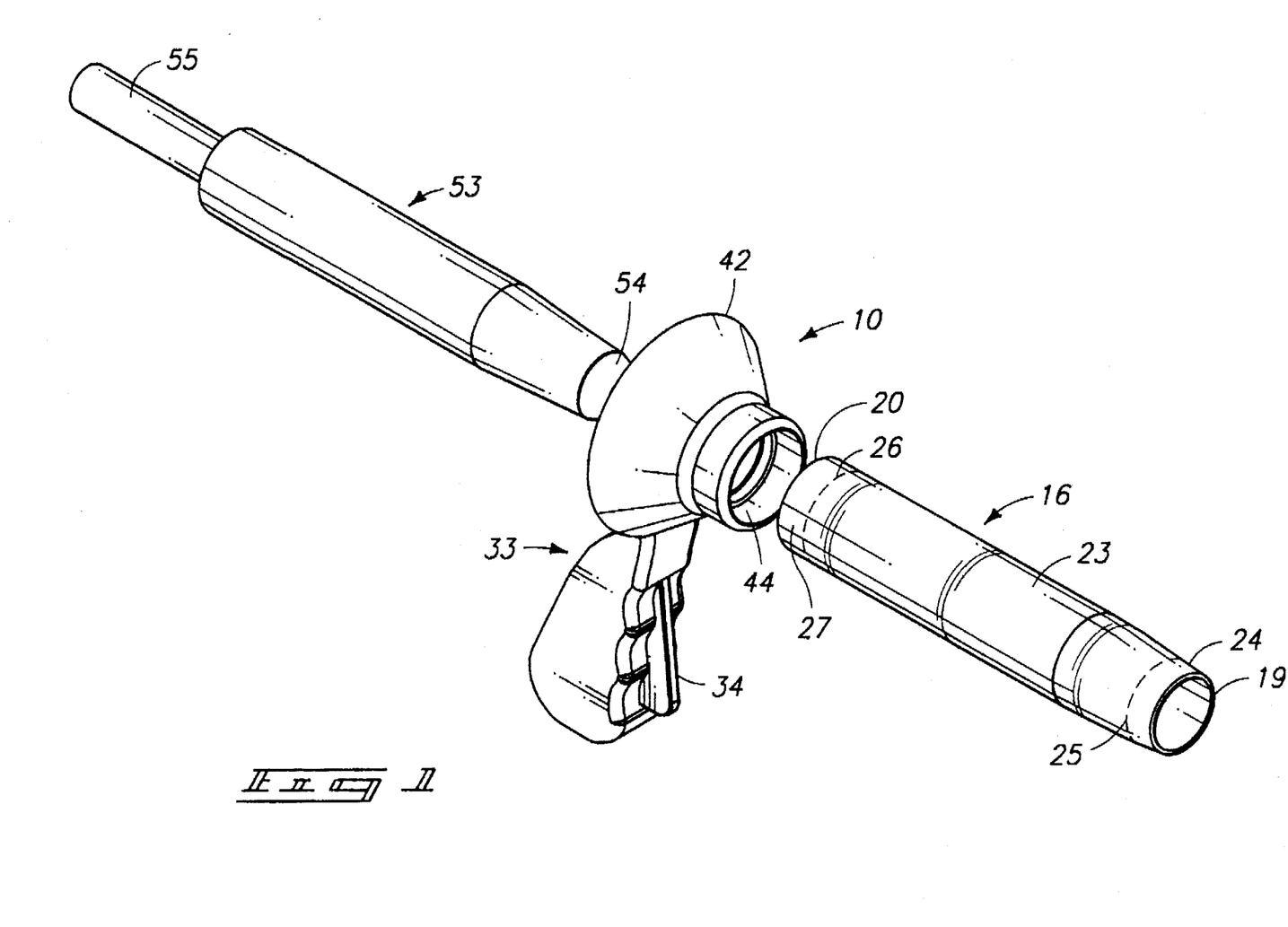
FIG. 1 is an exploded perspective view of a first preferred form of the present inflatable speculum, including a handle, and a stylet.
Figures 2, 3:
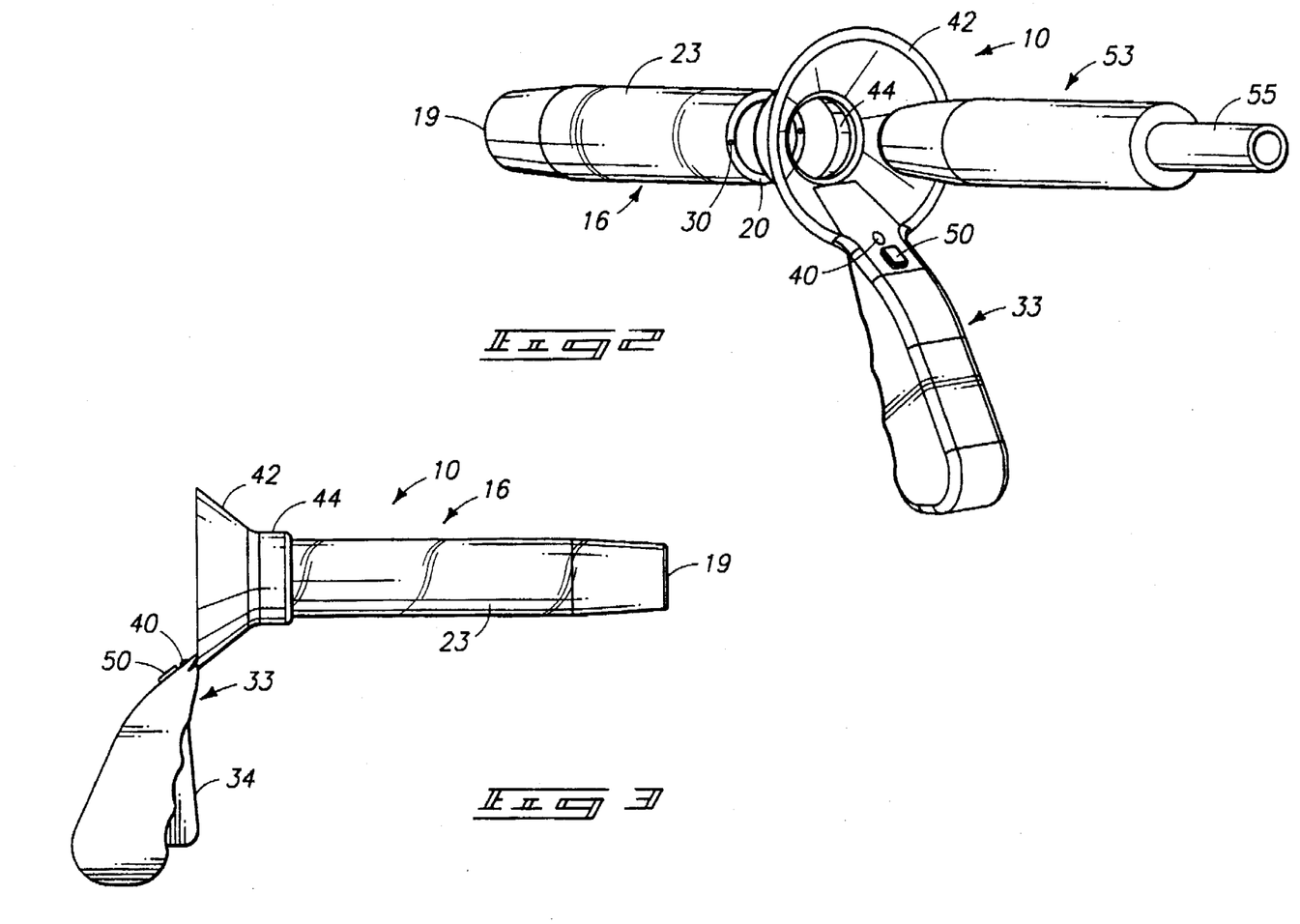
FIG. 2 is an exploded rear view of the first preferred form.
FIG. 3 is a side elevation view of the present speculum assembled with the handle and stylet in place.
Figure 4:
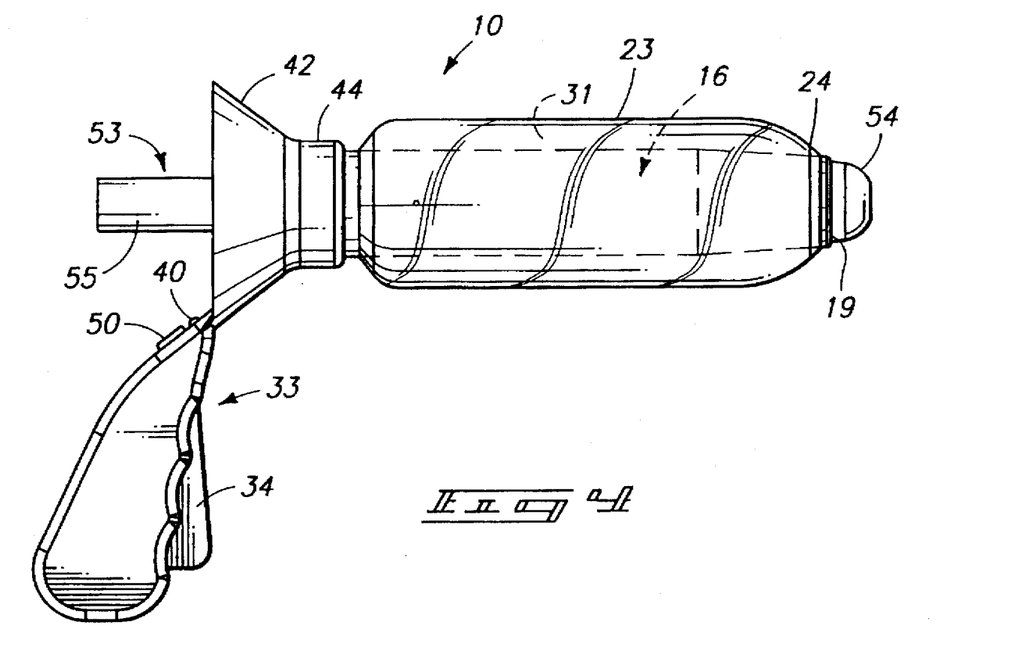
FIG. 4 is a side elevation view of the present speculum with the inflatable sleeve expanded.
Figure 5:
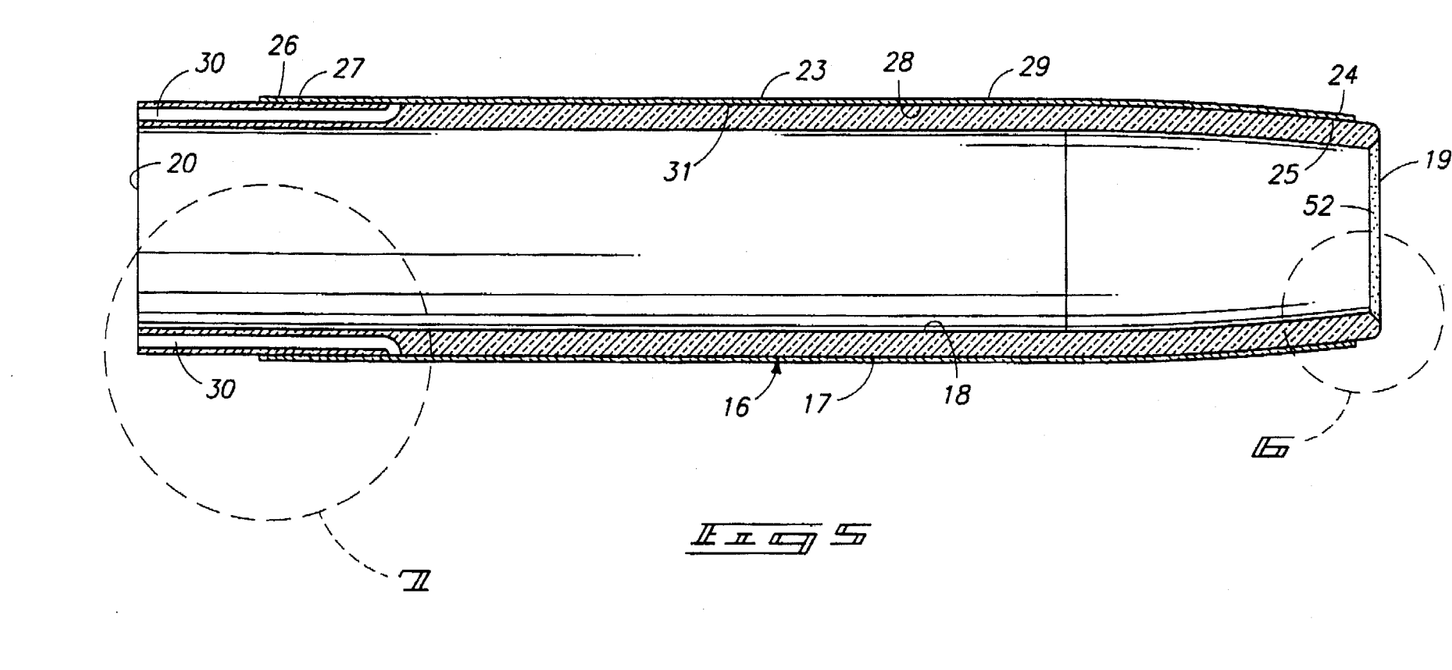
FIG. 5 is an enlarged sectional view of the tube and sleeve.
Figure 8:
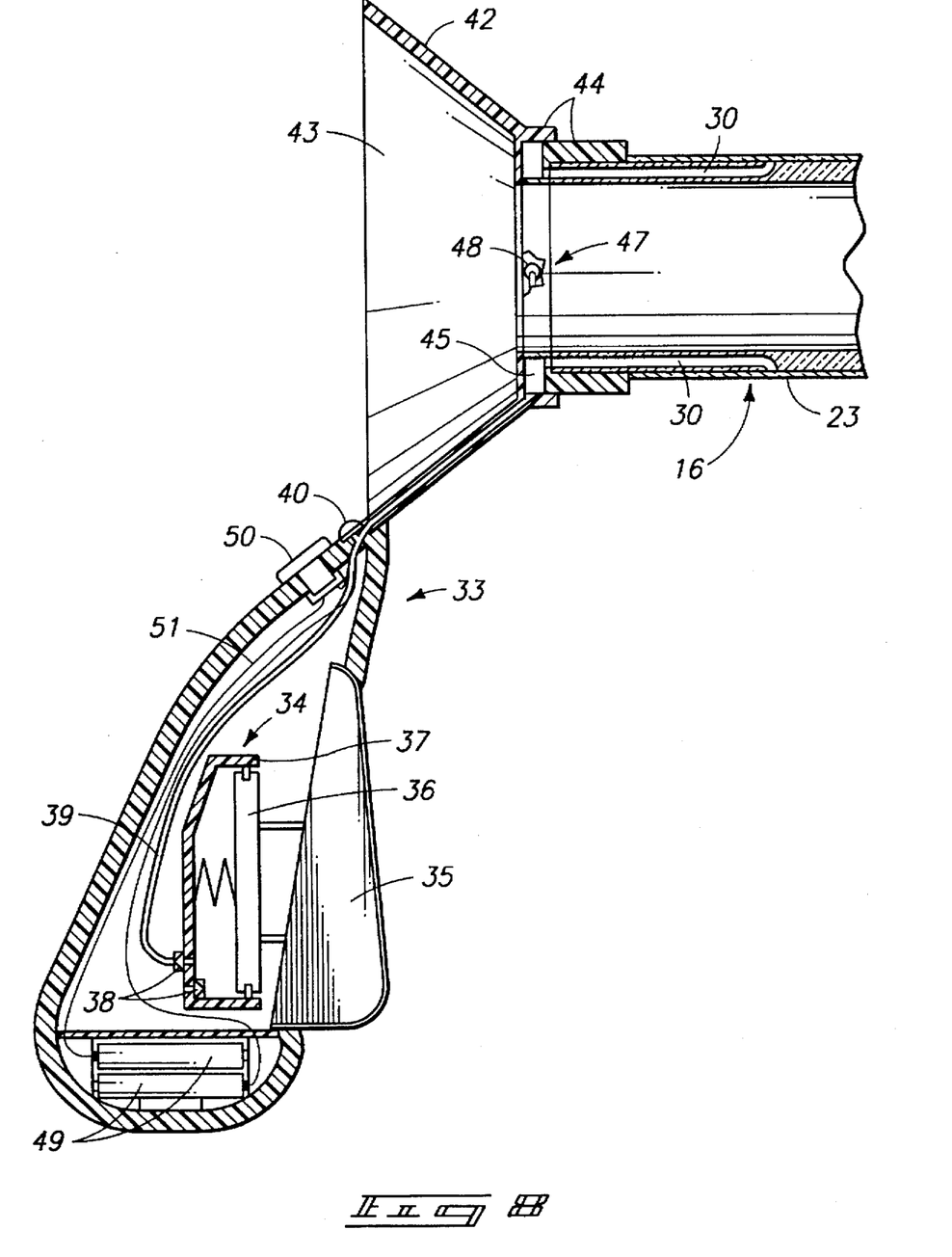
FIG. 8 is an enlarged sectional view of the handle and a portion of the tube mounted to the handle showing pumping and illumination elements.

In a preferred form, the handle also includes an eyepiece 42, formed as a conical flange 43 (FIGS. 2, 8). The conical flange shades the viewing area through the opening at its center, which is concentric with the bore of the first tubular member 16 (when mounted to the handle). The conical flange also will act as a stop, preventing inadvertent insertion of the tube beyond the tube length. Also at full insertion, the conical flange will hold adjacent tissues away from the viewing opening.

It is also pointed out as an alternative, that the conical flange could be produced as an integral part of the first tubular member, instead of the form shown herein where the flange is part of the handle. In this alternative form, the handle would be supplied with appropriate connections for mounting to the flange.

As illustrated, the preferred conical flange 43 leads to a cylindrical socket 44 that is shaped to receive the rearward end 20 of the first tubular member. The socket is made at a slightly larger diameter than the external surface diameter of the tube, to facilitate a releasable friction fit. Other conventional joint construction could also be used within the socket, such as threads, bayonet fittings and the like. However for simplicity, a friction fit is presently preferred. This allows the handle to be mounted at any angle about the central longitudinal axis of the tube. A circular open manifold 45 is defined within the socket (FIG. 8) joining the fluid line 39 to the fluid passages 30 in the tube. The friction fit will also assure an air-tight fit between the tube and handle so air will not leak from the fit between the socket and tube.

In a preferred form, the present invention also includes a light source 47 that may be provided within the handle 33. The light source, in general terms is operably connected to the first tubular member for directing light from the forward tube end 19. More specifically, the light source 47 is used to direct light along the tube and outwardly from the forward tube end, through the diffusion surface 52 described above.

The light source in the preferred example shown, includes an electric bulb 48 that is preferably positioned within the annular manifold 45 to light the rearward end of the tube, which in turn will transmit the light to and out the diffusion surface 52 at the forward tube end 19. To this end, and depending upon the material selected for the tube 16, the inside and outside surfaces may be coated with an inwardly reflective optic material to encourage light transmission along the tube, much in the same manner as fiber optics.

The bulb 48 is connected to one or more sources of current such as the batteries 49 shown in FIG. 8. It is noted at this point that other power sources, including rechargeable power packs, or appropriate alternating current connections may also be effectively used. In the example shown, appropriate conductors in a simple circuit 51 are provided to electrically connect the power source to the bulb. A simple on-off control switch 50 is provided in the circuit, mounted to the handle for easy access to selectively open and close the circuit to the bulb 48.

The stylet 53, briefly discussed above, is removably receivable axially within the bore of the first tubular member 16, with a tapered leading end 54 that when inserted into the tube bore will project axially to facilitate orifice penetration. The stylet 53 is provided with an outward surface that is of slightly smaller diameter than the bore of the tube, and slightly longer than the tube, to hold the tube rigid during insertion. A distal end 55 of the stylet projects rearwardly to facilitate insertion and removal of the stylet from the tube bore. It is pointed out as above, that the stylet is provided in different sizes, matching the various sizes of tube that may be provided either individually or in kit form.

The above constitutes a technical description of preferred forms of the invention. The following will describe, by way of example, use of the invention with particular reference to FIGS. 9–13.

Description of a preferred operation will begin assuming the attendant has a complete kit, including components exemplified in FIG. 13 to select from. Thus, given a selection of tube and stylet sizes, the attendant will first determine the desired tube size to use. This is done by experience and simple observation of the patient's physiology.

After a tube selection has been made, the associated stylet may be inserted into the selected tube so the tapered end projects slightly from the forward end of the tube. The tube may now be inserted using the distal end of the stylet as a handle, or, prior to insertion (as shown in FIG. 9) the tube is attached to the handle. This is done simply by inserting the rearward tube end in the handle socket. The handle can now be grasped during the insertion step.

Figure 10:
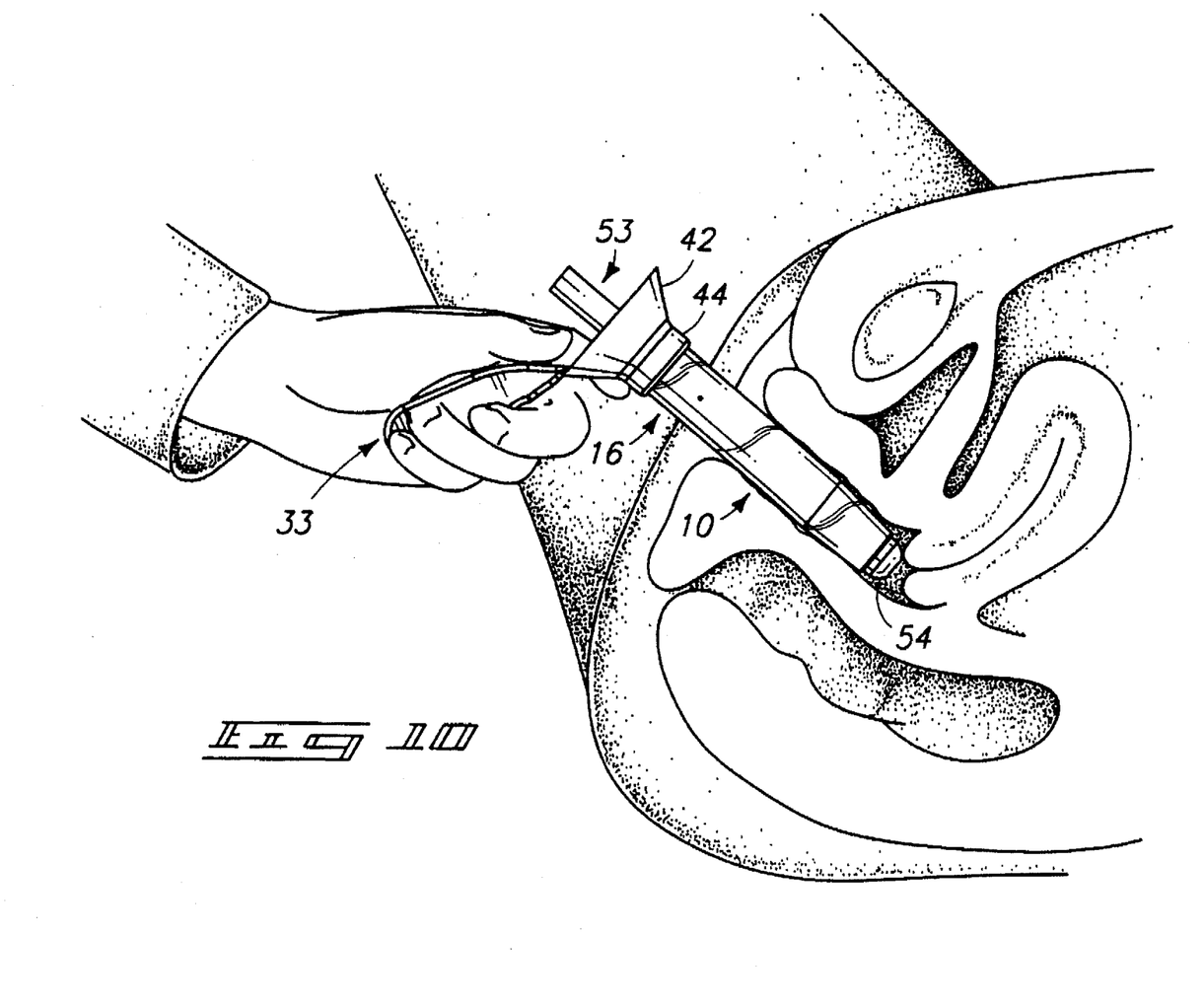

As the tube is inserted, the projecting tapered end of the stylet will gently penetrate the vaginal orifice. The tube is inserted full length if necessary, or until the tapered stylet end touches the cervix (FIG. 10). Now the stylet may be retracted, leaving the tube bore open to enable visual inspection.

Prior to, or more preferably after the stylet is retracted, the attendant may inflate the sheath. This is done simply by repeatedly squeezing the handle to operate the plunger and pump. Air will inflate the sheath (FIG. 11), expanding it to a larger diameter than that of the tube and dilating the vaginal canal. The external surface of the radially expanding sheath will engage and conform to all the adjacent tissues, thus providing a uniform dilating pressure, with no painful edges or hard, cold surfaces contacting the vaginal walls to cause discomfort to the patient. Further, the inflation process may occur over a period of time that is comfortable for the patient, so the vaginal canal is slowly dilated without sudden, often painful stretching of the sensitive tissues.

The inflation procedure is continued until the attendant is satisfied that the vaginal walls have been firmly and fully engaged by the inflated sheath. The entire speculum will now be easily supported by the surrounding tissues and will not require further support by the attendant's hand. This frees both of the attendant's hands for manipulating instruments (not shown) which may be inserted through the bore of the tube to facilitate examination or treatment.

Figure 12:
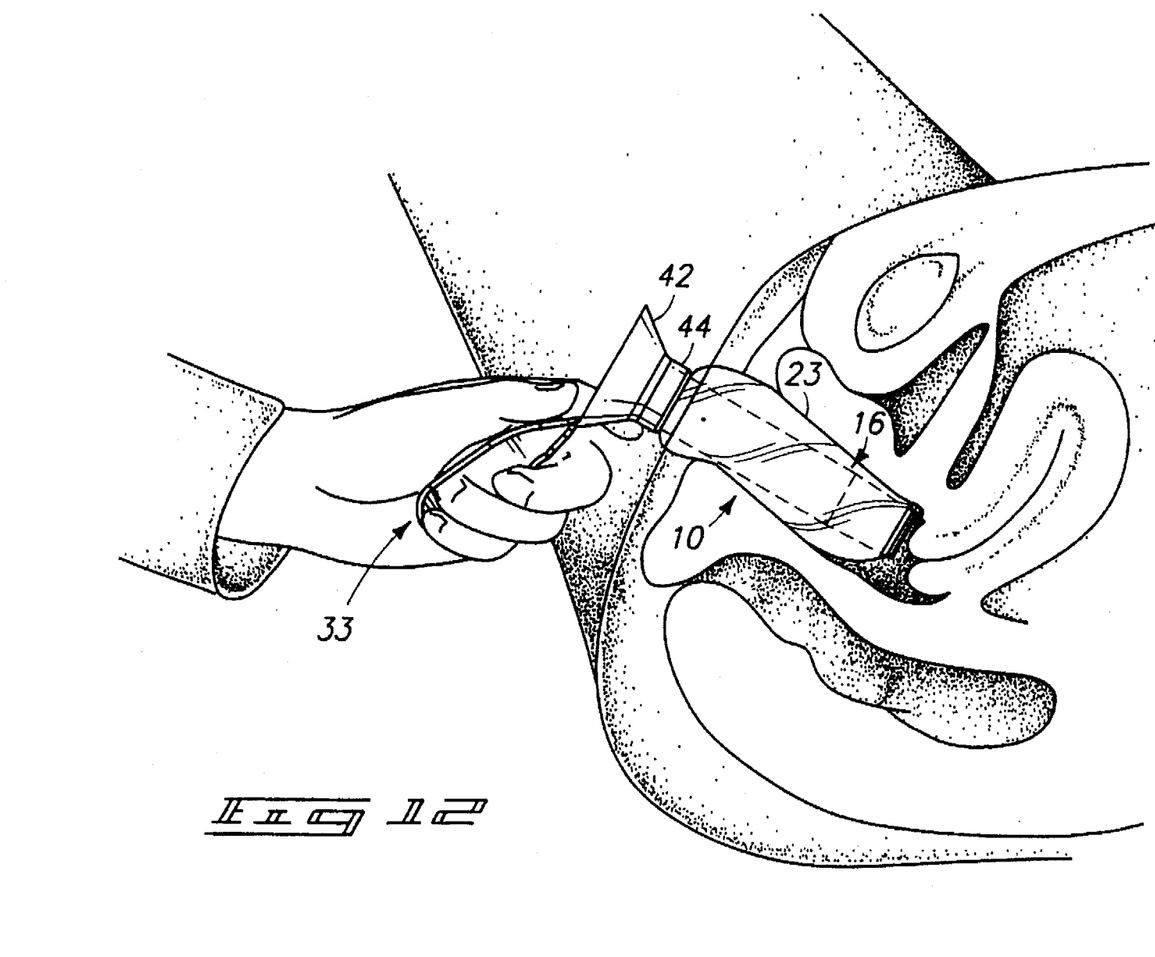

FIG. 12 exemplifies the degree of freedom the attendant has for manipulating the tube angularly within the vaginal canal, within the air cushion provided by the inflated sheath. In fact the tube can be manipulated relatively freely without moving the contact surface between the sheath and engaged tissues. This can be done without discomforting the patient since the tube is moving within the air cushion created between the tube and sheath and the engaged vaginal tissues remain relatively undisturbed.

At any time during the above procedure, the attendant may operate the switch to turn the light source on. The light produced from the bulb will be transmitted forwardly along the length of the tube and be emitted from the light diffusion surface at the forward tube end. Thus the interior tissues will be illuminated while the bore of the tube remains unobstructed.

Once the examination or treatment is completed, the attendant may simply press the release valve to deflate the sheath. The elastic material of the sheath will quickly return to its more relaxed condition adjacent the tube, allowing the tube to be easily retracted. This again may be done leisurely to minimize adverse sensation to the patient.

It is pointed out that the transparent nature of the sheath and tube will allow visual inspection of the vaginal walls, during insertion, at inflation of the sheath, and during retraction. This further aids the examination procedure by allowing full viewing of not just the cervix, but the entire physiology of the area concerned.

With selective use of the present speculum, the patient will appreciate the gentle treatment, and the attendant will experience a heretofore unknown ability to complete a thorough and complete examination or treatment in a relatively quick, efficient manner.

Following the examination or treatment, the tube can be removed from the handle and be discarded along with the associated stylet, leaving only the handle to be cleaned. Since the handle has had no internal contact, simple disinfecting and cleaning routines can be performed prefunctionary to the next examination or treatment with a fresh, sanitary, size selected tube member and matching stylet.

It is pointed out that the present speculum may be selectively used without the handle. Pressure to inflate the sheath may be applied by other sources such as conventional blood pressure cuff bulbs, or by other means that are convenient and accessible in medical facilities.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. An expandable speculum, comprising:
    a first elongated tubular member formed of a substantially rigid material and including a continuous external surface and an internal bore formed along a longitudinal axis and leading from an open rearward end to an annular open forward end;
    an elastic tubular sheath disposed axially over the external surface of the first elongated tubular member, leaving the forward end open and radially inflatable with respect to the first tubular member and said longitudinal axis in response to application of fluid pressure;
    the first tubular member and sheath being configured to enable insertion with the sheath in a deflated state into an orifice defined by a supportive tissue, and such that the sheath may be inflated in the orifice to engage and expand against tissues surrounding the orifice and thereby secure the speculum within the orifice while permitting angular movement of the first tubular member with respect to the inflated sheath and the supportive tissue.

2. An expandable speculum as claimed by claim 1 wherein the first tubular member is transparent.

3. An expandable speculum as claimed by claim 1 wherein the sheath includes a forward end and a rearward end and wherein the forward end is sealed to the first tubular member.

4. An expandable speculum as claimed by claim 1 wherein the sheath is formed of latex.

5. An expandable speculum as claimed by claim 1 wherein the sheath is formed of substantially transparent latex, and the first tubular member is transparent.

6. An expandable speculum as claimed by claim 1 further comprising a fluid passage formed in the first tubular member and leading to a space between the external surface and the sheath.

7. An expandable speculum as claimed by claim 1 further comprising a stylet removably receivable axially within the bore of the first tubular member, with a tapered leading end projecting axially from the first tubular member to facilitate orifice penetration.

8. An expandable speculum as claimed by claim 1 further comprising a light source operably connected to the first tubular member for directing light from the forward end.

9. An expandable speculum as claimed by claim 1 and further comprising a light passage formed along the first tubular member and leading to a light diffusion surface on the first tubular member at the forward end thereof.

10. An expandable speculum as claimed by claim 1 wherein the sheath includes at least one end in sealed engagement with the first tubular member and is radially inflatable in response to application of fluid pressure applied between the external surface and the sheath.

11. An expandable speculum as claimed by claim 1 further comprising a handle releasably attachable to the first tubular member.

12. An expandable speculum as claimed by claim 1 further comprising a handle releasably attachable to the first tubular member and wherein the handle includes a pump and a fluid supply line extendable to the sheath for selectively inflating the sheath.

13. An expandable speculum as claimed by claim 1 further comprising a handle releasably attachable to the first tubular member and wherein the handle includes:
    a pump;
    a fluid supply line extendable from the pump to the sheath for selectively inflating the sheath; and
    a release valve connected to the pump and fluid supply line and selectively operable to deflate the sheath.

14. An expandable speculum, comprising:
    a handle;
    an eyepiece on the handle;
    a first elongated tubular member releasably connected to the handle adjacent the eyepiece and formed of a substantially rigid material and including a continuous external surface and an internal bore formed along a longitudinal axis and leading from an open rearward end to an annular open forward end;

an elastic tubular sheath disposed axially over the external surface of the first elongated tubular member, leaving the forward end open and radially inflatable with respect to the first tubular member and said longitudinal axis in response to application of fluid pressure;

the first tubular member and sheath being configured for releasable attachment to the handle in such a manner that the eyepiece is in axial alignment with the internal bore of the first tubular member, and such that the tubular member and sheath may be inserted in an orifice defined by supportive tissues with the sheath in a deflated state, the sheath being inflatable in the orifice to engage and expand against the supportive tissues and thereby secure the speculum axially within the orifice while permitting angular movement of the handle and first tubular member with respect to the inflated sheath and the supportive tissue.

15. An expandable speculum as claimed by claim 14 and further comprising a light conductive passage leading to the forward end; and a light source in the handle connectable to the light conductive passage.

16. An expandable speculum as claimed by claim 14 wherein the first tubular member includes a light conductive passage leading to a light diffusion surface formed in the first tubular member at the forward end thereof; and a light source in the handle connectable to the light conductive passage.

17. An expandable speculum as claimed by claim 14 wherein the sheath includes a forward end and a rearward end and wherein said ends are sealed to the first tubular member, forming an annular chamber between the sealed ends.

18. An expandable speculum as claimed by claim 14 wherein the sheath is formed of latex.

19. An expandable speculum as claimed by claim 14 wherein the sheath is formed of substantially transparent latex, and the first tubular member is transparent.

20. An expandable speculum as claimed by claim 14 further comprising a fluid passage formed in the first tubular member and leading to a space between the external surface and the sheath; and wherein the handle includes a pump connectable to the fluid passage and manually operable to direct pressurized fluid to the space between the external surface and the sheath.

21. An expandable speculum as claimed by claim 14 wherein the first tubular member includes an axial length dimension between the forward and rearward ends thereof; and further comprising a stylet removably receivable axially within the bore of the first tubular member, with a tapered leading end projecting axially forward of the first tubular member forward open end to facilitate orifice penetration, and a distal end projecting rearwardly from the rearward end of the tubular member to permit axial insertion and removal of the stylet into and out from the first tubular member.

22. An expandable speculum as claimed by claim 14 further comprising an electric light on the handle and a light conductor on the first tubular member for directing light from the forward end, and a control switch on the handle for selectively operating the light.

23. An expandable speculum as claimed by claim 14 wherein the sheath includes at least one end in sealed engagement with the first tubular member and is radially inflatable in response to application of fluid pressure applied between the external surface and the sheath.

24. An expandable speculum kit, with component parts including:

a handle;

an eyepiece on the handle;

a set of first elongated tubular members, each releasably connectable to the handle adjacent the eyepiece and formed of a substantially rigid material and including an external surface and an internal bore formed along a longitudinal axis;

wherein the elongated tubular members in the set include various lengths and cross-sectional dimension at the external surfaces thereof;

elastic tubular sheaths disposed axially over the external surfaces of the first elongated tubular members and radially inflatable with respect to the first tubular members and said longitudinal axis in response to application of fluid pressure;

the first tubular members and associated sheaths being configured for selection according to a determined orifice size into which the a selected member and sheath are to be inserted and wherein any one of the members is releasably attachable to the handle in such a manner that the eyepiece is in axial alignment with the internal bore of said any one member;

and wherein said any one member and the sheath mounted thereto may be inserted in an orifice defined by supportive tissues, with the sheath in a deflated state, the sheath being inflatable in the orifice to engage and expand against the supportive tissues and thereby secure the speculum axially within the orifice while permitting angular movement of the handle and first tubular member with respect to the inflated sheath and the supportive tissue.

* * * * *